(12) United States Patent
Kostka et al.

(10) Patent No.: US 7,696,480 B2
(45) Date of Patent: Apr. 13, 2010

(54) METHOD AND APPARATUS FOR DETERMINING AN OBJECT MATERIAL

(75) Inventors: Guenther Kostka, Erlangen (DE); Peter Schmitt, Erlangen (DE); Andreas Jobst, Nuremberg (DE)

(73) Assignee: Fraunhofer-Gesellschaft zur Foerderung der angewandten Forschung e.V. (DE)

( * ) Notice: Subject to any disclaimer, the term of this patent is extended or adjusted under 35 U.S.C. 154(b) by 0 days.

(21) Appl. No.: 11/528,052

(22) Filed: Sep. 27, 2006

(65) Prior Publication Data

US 2007/0064868 A1 Mar. 22, 2007

Related U.S. Application Data

(63) Continuation of application No. PCT/EP2005/003447, filed on Apr. 1, 2005.

(30) Foreign Application Priority Data

Apr. 2, 2004 (DE) ........................ 10 2004 017 149

(51) Int. Cl.
*G01N 23/06* (2006.01)
(52) U.S. Cl. .................... 250/358.1; 378/53; 378/56
(58) Field of Classification Search ............. 250/358.1; 378/53, 56
See application file for complete search history.

(56) References Cited

U.S. PATENT DOCUMENTS 4,668,867 A * 5/1987 Lingenfelter ............. 250/358.1
4,910,757 A * 3/1990 Kiyasu et al. .................. 378/53
4,987,584 A * 1/1991 Doenges ....................... 348/82
5,481,584 A * 1/1996 Tang et al. .................. 378/98.9
5,838,758 A 11/1998 Krug et al.
6,449,334 B1 9/2002 Mazess et al.
2004/0197234 A1 10/2004 Endo et al.
2004/0218728 A1* 11/2004 Heismann .................... 378/207

FOREIGN PATENT DOCUMENTS

| GB | 1103591 | 2/1968 |
|---|---|---|
| GB | 2 365 522 | 2/2002 |
| WO | 01/86272 | 11/2001 |
| WO | 02/50521 | 6/2002 |

OTHER PUBLICATIONS

English Translation of PCT International Preliminary Report; PCTEP2005/003447; Jan. 4, 2005.

* cited by examiner

*Primary Examiner*—David P Porta
*Assistant Examiner*—Shun Lee
(74) *Attorney, Agent, or Firm*—Beyer Law Group LLP

(57) ABSTRACT

One finding of the present invention is that, by use of radiation with a polyfrequent effective spectrum for the examination of the object, beam hardening or shift of the spectrum's center of gravity does indeed lead to the fact that the effectively operative absorption coefficient or attenuation coefficient and/or the effective operative reflection coefficient of the object material, and thus particularly also the ratio of two coefficients to different radiation spectrums, no longer is solely specific for the material, but also depends on the thickness, but that this may be accepted, and nevertheless exact classification of the object material can still be done by using, in addition to the ratio of the absorption and/or reflection coefficients, one of the intensity values resulting during irradiations, in order to perform an association with one of a plurality of predetermined materials on the basis of reference data.

18 Claims, 4 Drawing Sheets

METHOD AND APPARATUS FOR DETERMINING AN OBJECT MATERIAL

CROSS-REFERENCE TO RELATED APPLICATION

This application is a continuation of co-pending International Application No. PCT/EP2005/003447, filed Apr. 1, 2005, which designated the United States and was not published in English and is incorporated herein by reference in its entirety.

BACKGROUND OF THE INVENTION

1. Field of the Invention

The present invention relates to the determination of an object material, such as it is used for the industrial sorting of materials. Such a sorting, for example, takes place in the separation of aluminum alloys of various kinds from the automobile scrap processing.

2. Description of the Related Art

In the recycling of scrap materials, such as metal alloys from automobile shredder companies, there is the necessity to employ material separation methods, because only materials of pure kind achieve a market value worth mentioning. For the separation of metals from non-metals, effective methods are known and in use. Moreover, methods for the separation of magnetic and of non-magnetic metal alloys are used. For the separation of various light metal alloys, for example aluminum or magnesium alloys, which only differ by the percentage of the alloy constituents, however, no or insufficiently reliable methods are in industrial use. With the increasing trend toward lightweight automobile construction, there is the increasing necessity for a reliable differentiation method for these materials.

A previous way for the recognition of different types of light metal alloys is mainly based on optical methods. Here, the surface color and the surface reflectance, as well as a characteristic shape of the shredder parts, are analyzed and associated with certain material types. One potential separation method for the subsequent separation of the materials, for example, consists in the use of mechanical impacts or of air pressure nozzles. But since the surface color of shreddered metal parts is no reliable, constant property due to potential pollution or other influences, a purely optical evaluation is highly likely to lead to a high false classification, and thus false sorting.

Hence, differentiation methods based on the combined evaluation of optical properties and X-ray transmission intensities have recently been proposed. In the laid-open publication WO 02/50521 A2, the use of a multiple energy method for the separation of various materials is described. Here, the objects moved on a conveyor belt are examined or radiated through one after the other by means of several arrangements of X-ray sources and line detectors at different X-ray lines or energies or wavelengths and analyzed with reference to the material-specific property by subsequent signal processing. In the signal evaluation, it is assumed that the characteristic quantity of assessment, namely the quotient Q of the attenuation coefficient $\mu$ at the different radiation energies is only material-dependent. Accordingly, the material determination is determined solely due to the ratio Q of the absorption coefficient $\mu$ at a first transmission energy level to the absorption coefficient $\mu$ at a different transmission energy level.

It is disadvantageous in the procedure proposed in WO 02/50521 A2 that a monochromatic effective transmission spectrum is used in the evaluation of the transmission image. Mono-energetic X-ray sources include isotopic radiators, for example. They may also be realized by the combined employment of X-ray tubes or synchrotron devices with monochromators. These monochromatic X-ray sources, however, have a series of specific disadvantages very strongly limiting the possibilities of their industrial-scale employment. The employment of synchrotron radiation generally has to be ruled out for the industrial employment. Monochromatized X-ray sources have a comparatively low radiation intensity, which leads to unfavorably long measurement durations and low throughput.

Therefore, there is a need for a determination scheme for object materials enabling quicker, more inexpensive, and, stated broadly, less intensive determination on the one hand, and nevertheless providing sufficient classification accuracy for the separation of various light metal alloys on the other hand.

SUMMARY OF THE INVENTION

It therefore is the object of the present invention to provide a determination scheme for object materials enabling less intensive object material determination with concurrently high classification accuracy, particularly also regarding light metal alloys.

In accordance with a first aspect, the present invention provides an apparatus for determining an object material of which an object consists, having: an irradiator-receiver pair for irradiating the object and receiving a resulting radiation with a first polyfrequent effective spectrum, transmitted through the object or reflected from the object, in order to obtain a first intensity value, and for irradiating the object and receiving a resulting radiation with a second polyfrequent effective spectrum, transmitted through the object or reflected from the object, in order to obtain a second value, wherein the first polyfrequent effective spectrum differs from the second polyfrequent effective spectrum; a provider for providing reference data for a plurality of predetermined materials; and a processor for associating the object material with one of the predetermined materials on the basis of the reference data, a combination value based on the first and the second information value, as well as at least the first or second intensity value.

In accordance with a second aspect, the present invention provides a method of determining an object material of which an object consists, with the steps of: irradiating the object and receiving a resulting radiation with a first polyfrequent effective spectrum, transmitted through the object or reflected from the object, in order to obtain a first intensity value; irradiating the object and receiving a resulting radiation with a second polyfrequent effective spectrum, transmitted through the object or reflected from the object, in order to obtain a second value, wherein the first polyfrequent effective spectrum differs from the second polyfrequent effective spectrum; providing reference data for a plurality of predetermined materials; and associating the object material with one of the predetermined materials on the basis of the reference data, a combination value based on the first and the second information value, as well as at least the first or second intensity value.

In accordance with a third aspect, the present invention provides a computer program with program code for performing, when the computer program is executed on a computer, a method of determining an object material of which an object consists, with the steps of: irradiating the object and receiving a resulting radiation with a first polyfrequent effective spectrum, transmitted through the object or reflected from the object, in order to obtain a first intensity value;

irradiating the object and receiving a resulting radiation with a second polyfrequent effective spectrum, transmitted through the object or reflected from the object, in order to obtain a second value, wherein the first polyfrequent effective spectrum differs from the second polyfrequent effective spectrum; providing reference data for a plurality of predetermined materials; and associating the object material with one of the predetermined materials on the basis of the reference data, a combination value based on the first and the second information value, as well as at least the first or second intensity value.

An inventive method for determining an object material of which an object consists includes irradiating the object and receiving a resulting radiation transmitted through the object or reflected from the object with a first polyfrequent effective or effectively acting spectrum, in order to obtain a first intensity value; irradiating the object and receiving or detecting a resulting radiation transmitted through the object or reflected from the object with a second polyfrequent effective spectrum, in order to obtain a second value, wherein the first polyfrequent effective spectrum differs from the second polyfrequent effective spectrum; as well as providing reference data for a plurality of predetermined materials. Finally, the object material is associated with one of the predetermined materials on the basis of the reference data, a combination value based on the first and the second information value, as well as at least the first or second intensity value. The reference data may have been acquired from trial measurement on samples of the known predetermined materials or from simulations or calculations.

One finding of the present invention is that, by use of radiation with a polyfrequent effective spectrum for the examination of the object, beam hardening or shift of the spectrum's center of gravity does indeed lead to the fact that the effectively operative absorption coefficient or attenuation coefficient and/or the effective operative reflection coefficient of the object material, and thus particularly also the ratio of two coefficients to different radiation spectrums, no longer is solely specific for the material, but also depends on the thickness, but that this may be accepted, and nevertheless exact classification of the object material can still be done by using, in addition to the ratio of the absorption and/or reflection coefficients, one of the intensity values resulting during irradiations, in order to perform an association with one of a plurality of predetermined materials on the basis of reference data.

In other words, the central idea of the present invention consists in the following considerations. A necessary prerequisite for the assumption from the above-cited WO 02/50521 A2 that the characteristic quantity of assessment, namely the quotient of the attenuation coefficient of the different radiation energies, was only material but not thickness-dependent, is that the spectrum of the transmitting X-ray radiation does not dependent on the radiated-through thickness of the object. In fact, this is only the case when the radiation sources provide mono-energetic radiation. Otherwise, the so-called beam hardening develops with increasing transmission thickness. In other words, with the use of industrial X-ray sources without monochromator, the prerequisite of the constancy of the coefficient of the attenuation coefficient Q is not given. Instead, a so-called beam hardening of the X-ray radiation captured by the detector develops. Here, with increasing transmission length or depth, the proportion of for example higher-energy X-ray radiation rises in proportion to the proportion of lower-energy radiation due to the higher penetration capability. Thereby, a shift of the effective attenuation coefficient for the respective measurements at different radiated-through thickness, and thus a thickness-dependent shift of the absorption coefficient quotient Q results. This leads to the fact that various materials may be associated with one and the same Q value, and thereby can no longer be separated uniquely. This is particularly disadvantageous in the separation of very similar metal alloys differing only by the amount and type of the admixtures, for example in the separation of cast aluminum and knead aluminum alloys, which are both provided from the automobile shredder companies at the same time, but which can only be recycled separately from each other.

According to the present invention, however, it is benefited from the disadvantage of the beam hardening when using polyfrequent radiation, so that a virtue is made of necessity, so to speak. According to the invention, for enabling a classification of object materials, it is now in fact not started from a fixed, thickness-independent quotient of the absorption coefficients, but the beam hardening, for example, at the transmission of the X-ray radiation through the materials to be examined is taken into account. The thickness dependence of the ratio of the transmission and/or reflection coefficients is taken into account, according to the invention, by using, in addition to a combination value of a value based on the first intensity value and a value based on the second intensity value, namely in a special example, the coefficient of the logarithm of the two intensity values, at least also the first or second intensity value itself for the association of the object material with one of the predetermined materials.

The improvement made as opposed to the procedure described in WO 02/50521 A2 consists, among other things, in the fact that it is possible to utilize industrial, polychromatic X-ray tubes as radiation sources, wherein the effect of the beam hardening occurring here does not have any negative influence on the differentiation possibility of similar materials. The method proposed here leads to a unique differentiation of materials in spite of polychromatic radiation. Industrial X-ray sources, as opposed to monochromatized sources, except for synchrotron radiators, provide a very high number of X-ray quantums per time, so that when employing an X-ray camera with a multiplicity of picture elements or pixels, the integration time of the X-ray detector can be very short and the spatial resolution of the detector very high. Thereby, high material throughput and differentiation of small particles are achieved. Moreover, a multiplicity of measured values concerning a sample can be obtained at the same time.

BRIEF DESCRIPTION OF THE DRAWINGS

These and other objects and features of the present invention will become clear from the following description taken in conjunction with the accompanying drawings, in which.

DESCRIPTION OF THE PREFERRED EMBODIMENTS

Figure 1:
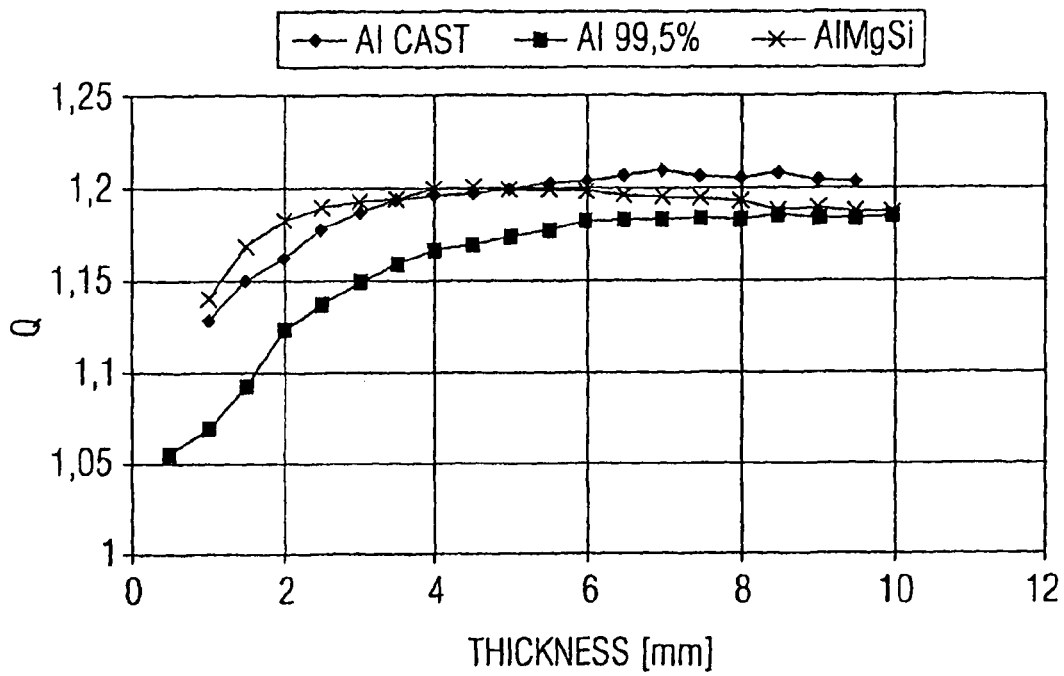
FIG. 1 is a diagram in which the Q value is plotted versus the material thickness for three similar aluminum alloys.

Before explaining preferred embodiments of the present invention on the basis of the figures in greater detail in the following, it is pointed to the fact the subsequent embodiments only exemplarily refer to the transmissive X-ray examination, but that the present invention may also be applied to other examination types in which material is to be differentiated by transmission or reflection of polychromatic radiation and in which a shift of the center-of-gravity energy, and thereby a shift of the effective interaction coefficient, such as the absorption or reflection coefficient, arise by different interaction coefficients.

On the basis of FIGS. 1 and 2, at first the basics necessary for understanding the material determination according to the embodiments described in the following will be explained. It is the aim of the material determination according to the subsequent embodiments to associate the material of an object with a material from a predetermined plurality of predetermined materials. To this end, according to these embodiments, at least two transmissions of the object with polychromatic X-ray radiation with different polychromatic radiation spectrums are performed. Due to the polychromatic examination, the beam hardening mentioned above and discussed in greater detail in the following arises. This beam hardening provides for the ratio of the effective attenuation coefficients to the two transmissions to be thickness-dependent. The association of the object material with one of the predetermined materials is therefore performed, according to these embodiments, using not only the ratio of the logarithm of the two intensity values, but also using one of the two intensity values themselves, as it will be described in the following.

In the polychromatic X-ray transmission of material with a certain thickness d, the intensity I follows the exponential Lambert's attenuation law:

$$I = \int I_0(E) \cdot \exp(-\mu(E) \cdot \rho \cdot d) dE$$

wherein $I_0(E)$ is that intensity with which the material has been irradiated, $\mu(E)$ designates the energy-dependent, material-specific attenuation coefficient of the material to be examined, $\rho$ the material density of the material to be examined, and E a parameter of the radiation energy.

If this equation is simplified for the monochromatic case, the integration over the energy is eliminated, and the intensity I results as $$I = I_0(E) \cdot \exp(-\mu(E,d) \cdot \rho \cdot d)$$

wherein in both formulas, strictly speaking, d designates the thickness of the material to be examined in beam direction at the location at which the material is radiated through.

The attenuation coefficient $\mu(E,d)$ appears as a thickness-dependent effective absorption coefficient in the simplified second equation.

If two different polychromatic X-ray spectrums are used, such as by using two different X-ray tubes with different acceleration voltages, an intensity $I_1$ for a first X-ray tube acceleration voltage and an intensity $I_2$ for a different second X-ray tube acceleration voltage are obtained hereby. If the material is transilluminated at the same location or if the material has uniform thickness, $I_1$ and $I_2$ may be indicated with $I(E_1,d)$ and $I(E_2,d)$, respectively, according to the above simplified formula, wherein $E_1$ designates a mean effective radiation energy of the first polychromatic spectrum and $E_2$ a mean effective radiation energy of the second polychromatic spectrum, for example.

By taking the logarithm and dividing the measured intensities at the two different X-ray tube acceleration voltages, the material density $\rho$ and the material thickness d are eliminated, but not the thickness dependence of the effective absorption coefficient $\mu(E,d)$ in the above simplified formula. Thus, the material-specific and thickness-dependent quotient $Q(E_{1,2},d)$ results as $$\frac{\ln(I(E_1,d))}{\ln(I(E_2,d))} = \frac{\mu(E_1,d)}{\mu(E_2,d)} \equiv Q(E_{1,2},d)$$

FIG. 1 shows a plot of the calculated value $Q(E_{1,2},d)$ versus the material thickness d in units of mm for three different similar aluminum alloys, namely cast aluminum (Al cast), an alloy with an aluminum percentage of 99.5% (Al 99.5%), and an aluminum-magnesium-silicon alloy (AlMgSi). The intensity values $I(E_1,d)$ and $I(E_2,d)$ underlying the calculated values Q were obtained by irradiations with an X-ray tube, wherein a different X-ray tube acceleration voltage was used for the generation of the X-ray radiation, namely an X-ray tube acceleration voltage of 100 kV one time and an X-ray tube acceleration voltage of 130 kV the other time. In particular, the characteristic curves for the different alloys obtained in FIG. 1 were obtained on the basis of real measurements on samples with varying thickness. The measurement points are indicated with rhombs, squares, and crosses for the different aluminum alloys of Al cast, Al 99.5%, and AlMgSi, respectively, in FIG. 1, and the characteristic curves were obtained by connecting the individual measurement points.

It can be seen from FIG. 1 that the value $Q(E_{1,2},d)$ cannot uniquely be associated with certain materials, because this value varies with the thickness. The variations over the thickness are caused by the fact that, due to the beam hardening, the effective attenuation coefficients $\mu(E_1,d)$ and $\mu(E_2,d)$, as they result for the different acceleration voltages, are thickness-dependent, with a different dependence on the thickness. With increasing thickness, the spectrum of the radiation arriving at the detector becomes increasingly monochromatic due to the beam hardening, so that the quotient of the two effective attenuation coefficients $\mu$ reaches saturation, as it can be seen in FIG. 1 at greater thicknesses. How quickly the individual characteristic curves reach saturation, depends on how much the energy-dependent absorption coefficient of the material to be examined varies on the energy $E_1$ and/or $E_2$. Hereby, the characteristic curves for the different materials result.

So as to now remedy the supposed disadvantage that the value $Q(E_{1,2},d)$ alone is not suited for the unique determination of the material, an evaluation scheme based on a dual energy evaluation, which enables a unique association of measured intensity values with certain, previously learned materials, is used in the following embodiments. Here, as it will be described in greater detail in the following, value triplets T or value tuples P are formed from one or both measured individual intensities $I(E_1,d)$ and $I(E_2,d)$ at the different acceleration voltages or at other different conditions leading to a different effective transmission spectrum, and from the quotient of the effective absorption coefficients, which in turn is deduced from both intensity values. An example for the value triplet T is $T(I(E_1,d), I(E_2,d), Q(E_{1,2},d))$. An example for a value tuple P is $P(I(E_1,d) \; Q(E_{1,2},d))$.

Figure 2:
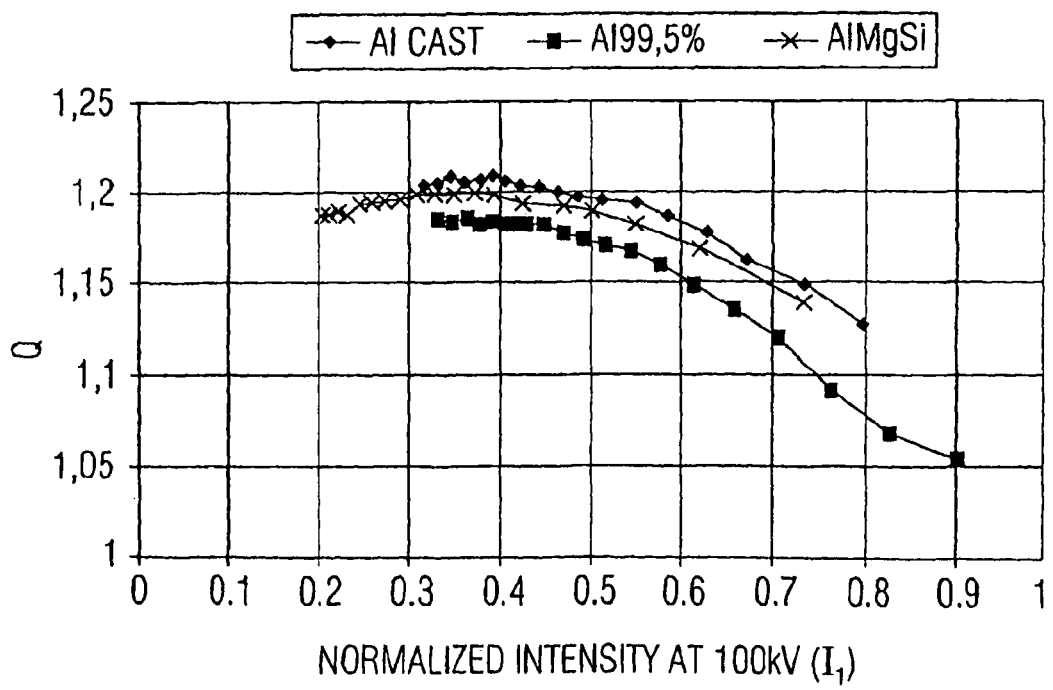
FIG. 2 is a diagram in which the Q value for the three aluminum alloys of FIG. 1 is plotted versus the normalized transmitted intensity at the lower tube acceleration voltage.

In FIG. 2, a plot of the values $Q(E_{1,2},d)$ of FIG. 1 versus the primary individual intensity $I(E_1,d)$ at the tube voltage $E_1$ is now shown. The measurement points are again indicated with rhombs, squares, and crosses and connected to each other so as to form characteristic curves for the individual materials.

The variations recognizable in the curves are due to statistical fluctuations of the number of X-ray quantums in the X-ray detector pixels and may be decreased significantly by signal averaging, for example.

From the illustration in FIG. 2, it becomes clear that the value triplets T and/or the value tuples P may be calibrated as characteristic curves and differentiated for all various potential materials and material thicknesses. In other words, the Q values $Q(E_{1,2},d)$ can be obtained and provided as reference data for two tube voltages $E_1$ and $E_2$ used, for materials of interest, and varying the material thickness d. In subsequent measurements on unknown samples or objects, according to subsequent embodiments, value triplets T or value tuples P were generated, using the same calculation rules as those described previously for the calculation of Q, and associated with the known materials by numerical comparison methods, such as the one the characteristic curve of which the value triplets or value tuples come closest to. Of course, the principle also works using only value tuples, namely the value tuples $(Q(E_{1,2},d), I(E_1,d))$ and $(Q(E_{1,2},d), I(E_2,d))$. In this case, the reference data, for example, correspond to the characteristic curves of FIG. 2 for the predetermined materials of interest. The association then takes place, for example, by an unknown material with unknown thickness d, for which the value pair $(Q(E_{1,2},d), I(E_1))$ was obtained with the acceleration voltages $E_1$ and $E_2$, being associated with that material the characteristic curve of which lies closest to this value pair in the graph of FIG. 2.

In contrast to the procedure according to WO 02/50521 A2 described in the introductory section of the description, which does indeed assume a thickness-independent Q value, the subsequent embodiments may thus take advantage of the fact that objects typically have a thickness variation, so that an entire range of value triplets and/or value tuples is available for the numerical comparison with the reference data for the evaluation for an object. For one object, not only one value tuple P or value triplet T is obtained, but many of such value tuples or triplets for different thicknesses. In turn, this means that the classification of an object material does not have to be performed only via an individual point or an individual value tuple or value triplet, but can be performed via a comparison of a whole series of value tuples or value triplets for different thicknesses with the characteristic curves of the different predetermined materials. Thereby, the accuracy and reliability of the determination schemes of the subsequent embodiments increases.

After having previously described the basics of the procedure in the material determination of the embodiments described in the following, with reference to FIGS. 3a-4, various embodiments for the material determination using an X-ray transmission will be described somewhat more concretely in the following, and with reference to FIG. 5 finally an embodiment for the application of a material determination in a material sorting equipment.

Figure 3A:
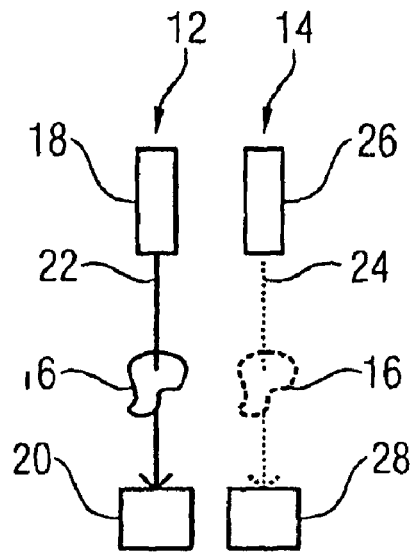
FIGS. 3a-3d are schematic drawings of possible arrangements for the transmissive examination of an object according to embodiments of the present invention.
Figure 3B:
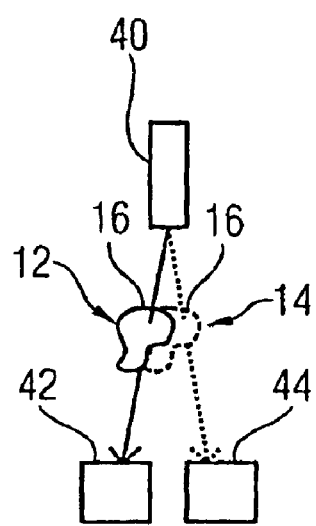
Figure 3C:
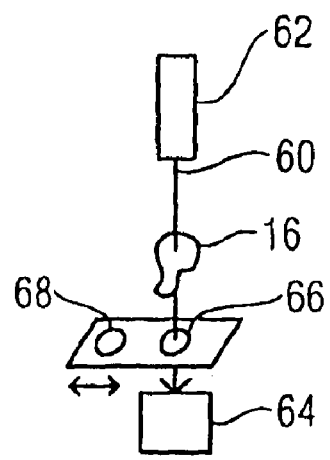
Figure 3D:
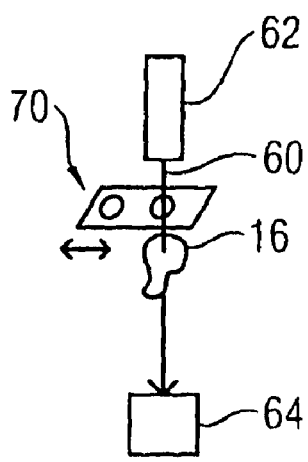
Figure 4:
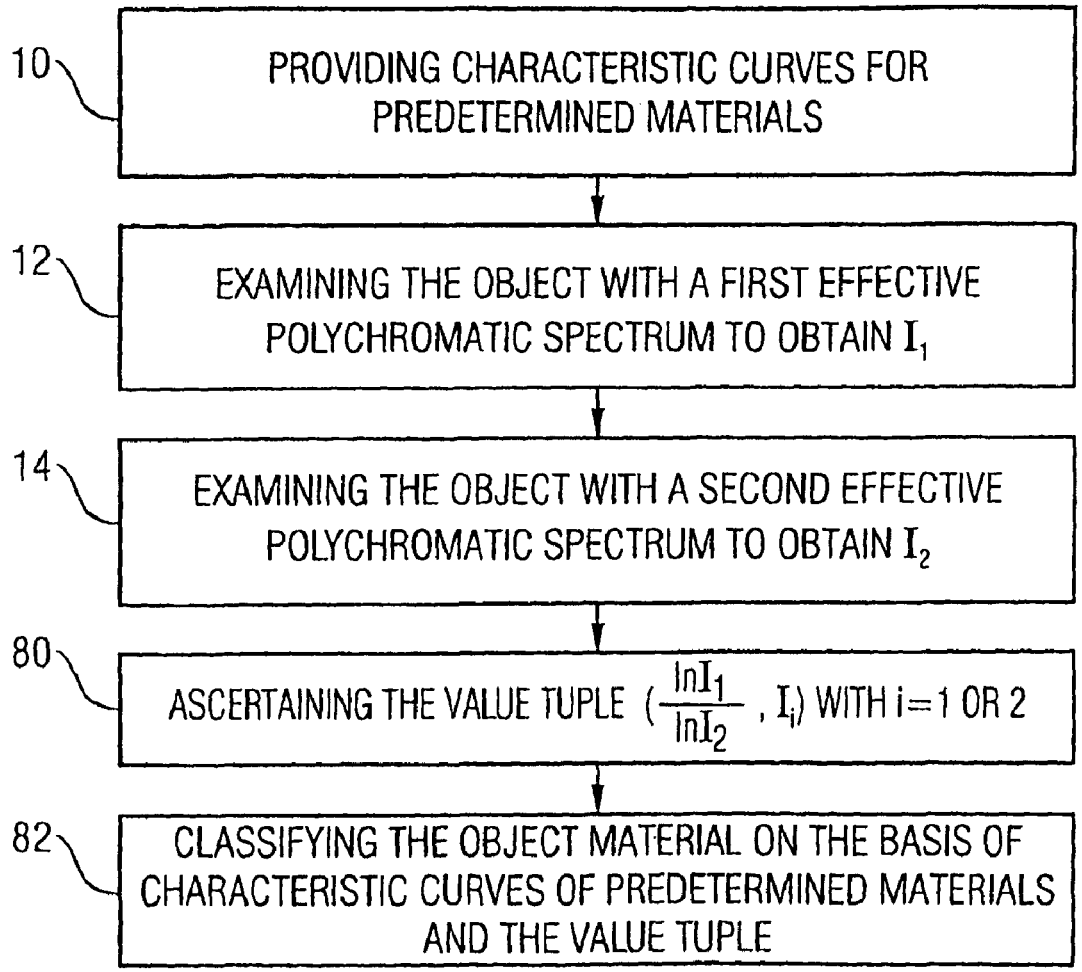
FIG. 4 is a flow chart for the illustration of the procedure in the classification of an object material according to an embodiment of the present invention.

Among FIGS. 3a-4, FIG. 4 shows the sequence of steps for the material determination or material classification, wherein in the description of the procedure according to FIG. 4 reference is made to FIGS. 3a-3c, which show various possible arrangements for the transmission of an object with different polyfrequent radiation spectra.

For the material determination of an object of unknown material to be examined or for the classification of the object material, in a step 10, at first characteristic curves are provided for a plurality of predetermined, known materials. The provision may include storing the data defining the characteristic curves just as well as generating these characteristic curves by performing measurements on the predetermined materials, as described previously with reference to FIG. 2. The characteristic curves are stored either in analytical form or using checkpoints or measurement points, as it is shown in FIG. 2.

For the generation of the characteristic curves, several measurements have been performed for each predetermined material, as described with reference to FIG. 2. Each measurement was performed at a different and not necessarily known thickness of the predetermined material. For example, a known material was simply scanned and thus transilluminated at differently thick locations. Each measurement included the transmission of the material with a first polyfrequent spectrum of the energy $E_1$ and a second polyfrequent spectrum of the energy $E_2$, so that each measurement yielded two intensity values $I(E_1,d)$ and $I(E_2,d)$ at the respective, if necessary, unknown thickness d. The result of the measurements for a predetermined material was then summarized into a series of tuples P or triplets T, which will in general sometimes also be referred to as vectors in the following. The vectors for a predetermined material are given by: $(I(E_1,d_i), Q(E_{1,2},d_i))$, $(I(E_2,d_i), Q(E_{1,2},d_i))$, or $(I(E_1,d_i), (Q(E_{1,2},d_i))$, wherein the values $d_i$ indicate the thicknesses having been radiated through in the different measurements i on the predetermined material, and i is an index for the measurement number. The first-mentioned case that only one tuple P of the intensity $I(E_1,d)$ and of the quotient $Q(E_{1,2},d)$ was used for each thickness measurement on a predetermined material, has been illustrated in FIG. 2. In this case, the characteristic curve thus is a one-dimensional function defined over an intensity, namely the intensity $I_1$ or $I(E_1,d)$ measured at the radiation energy $E_1$. In the case of the use of value triplets, the characteristic curve is a line passing in a three-dimensional space, at the three space axes of which the intensity $I_1$, the intensity $I_2$, and the value Q are plotted, respectively. As already mentioned, either only these checkpoints for the definition of the characteristic curves may be provided, or interpolations or parameters for analytical approximation functions for these characteristic curves are provided. With reference to step 10, it is again explicitly pointed to the fact that, in the different measurements with reference to one and the same predetermined material, the thickness just radiated through of the material does not have to be known. Characteristic curve data may also be generated with an object of a known material, which has different thicknesses, and unknown thicknesses in particular.

At this point, it is to be pointed out that the step 10 does not necessarily have to be executed. It is possible, after all, that the characteristic curve or reference data are generated in advance, i.e. by a simulation, or computationally, i.e. by a calculation. Here, the simulation may completely simulate the transmission process. Furthermore, it is also possible, however, that characteristic curve data for another material are deduced by simulation or calculation, such as interpolation or extrapolation, starting from characteristic curve data obtained for a first predetermined material by measurement.

In a step 12, the object to be examined is now examined with the first effective polyfrequent spectrum, as it also has been used for the generation of the characteristic curve data in step 10, and which corresponds to the energy $E_1$, for example. In the step 12, an intensity value $I_1$ is obtained, with $I_1=I(E_1,d)$, wherein d is the thickness of the object at the transmission location. In a step 14, the object is then examined with the second effective polyfrequent spectrum, which has also already been used in the measurements in step 10 and corresponds to the energy $E_2$. In the step 14, the intensity value $I_2$ or $I(E_2,d)$ is obtained.

FIGS. 3a-3c show various possibilities for performing the steps 12 and 14. FIG. 3a shows the object 16 to be examined in solid lines, as it is placed between an arrangement of X-ray source 18 and an X-ray detector 20 in the optical train 24. In this manner, the examination is performed after step 12. In step 12, a first X-ray tube acceleration voltage in the X-ray source 18 is used. FIG. 3a shows the object 16 in a state during the second examination step 14 in dashed lines. In this state, the object 16 is arranged in the optical train 22 between a further X-ray source 26 and a further X-ray detector 28. The X-ray source 26 uses an X-ray tube acceleration voltage different from that of the X-ray source 18. With this, the spectrum with which the object 16 is transilluminated in the steps 12 and 14 differs. The X-ray detectors 20 and 28, for example, are identical in the embodiment in FIG. 3 and are sensitive to both the X-ray spectrum of the source 18 and the X-ray spectrum of the source 26. According to the embodiment of FIG. 3a, a polyfrequent transmission of the object 16 with different polyfrequent spectrums is achieved in this manner.

The embodiment of FIG. 3a may be altered in that one and the same pair of X-ray source 18 and X-ray detector 20 is used for performing the steps 12 and 14. In this case, only the X-ray tube acceleration voltage is changed between the steps 12 and 14, whereby the deceleration spectrum of the then only X-ray source changes between the steps 12 and 14. Furthermore, it would be possible that the X-ray detectors 20 and 28 have different sensitivities in the embodiment of FIG. 3a, namely that the X-ray detector 20 is more sensitive to the X-ray radiation of the X-ray source 18 and the X-ray detector 28 to the X-ray radiation of the X-ray source 26. The effective polyfrequent radiation spectrum in the step 12 is defined, for example, as the product of the X-ray spectrum used for the irradiation and the sensitivity course or the sensitivity characteristic curve of the associated X-ray detector.

FIG. 3b shows an alternative arrangement to FIG. 3a. In this arrangement, the object 16 is irradiated by one and the same X-ray source 40, which also uses the same acceleration voltage in both steps 12 and 14, both in step 12, which is illustrated in solid lines, and in step 14, which is indicated by dashed lines. With this, the X-ray spectrum used for irradiation is the same in both steps. But the X-ray radiation passing through the object 16 is detected by an X-ray detector 42 in step 12 and by another X-ray detector 44 in step 14, the two X-ray detectors 42 and 44 having different sensitivity characteristic curves. The latter is achieved by use of filters in the X-ray detectors 42 and 44, for example.

Alternatively, the different sensitivity is achieved by the use of different sensing materials in the detectors 42 and 44. Again, another possibility consists in using different discriminators in the case of directly converting detectors 42 and 44, such as those based on GaAs, with otherwise the same physical construction. Directly converting detectors are formed such that arriving X-ray quantums generate pulse amplitudes in the detection signal in the individual signals of the detectors, which are then counted in the detectors 42 and 44, in order to obtain counter values, which then represent or indicate the above-mentioned intensity values $I_1$ and/or $I_2$, i.e. the actual output signals of the detectors. In this, every such detector uses a so-called discriminator, i.e. a threshold value, in order to count only pulses with such pulse amplitudes exceeding the predetermined threshold value. The height of the pulse amplitudes, however, varies with the energy of the arriving quantums. Thus, the energy discrimination may for example be achieved by employing suitably different discriminators for the discrimination of the pulse amplitudes generated by the X-ray quantums in directly converting detectors 42 and 44.

In the embodiment of FIG. 3b, in spite of the use of the same irradiation spectrum in the steps 12 and 14, a different effective polyfrequent transmission spectrum therefore results, because the X-ray detectors 42 and 44 are differently sensitive at higher or lower X-ray energies.

According to the embodiment of FIG. 3c, the object 16 is placed in an optical train 60 between an X-ray source 62 and an X-ray detector 64 in both steps 12 and 14, with the same acceleration voltage being used in the X-ray source 62 in both steps. But one of two filters 66 and/or 68, which have different filter characteristic curves, is connected into the optical train 60 either behind the object 16 or before the X-ray detector 64. Between the subsequent steps 12 and 14, the respective other filter is then slid into the optical train 60 or the filter is changed. Alternatively, the filters 66 and 68 could also be placed into the optical train 60 before the object 16, i.e. between the X-ray source 62 and the object 16. This is shown at 70 in FIG. 3D.

Instead of a successively performed intensity value detection according to FIG. 3c, an X-ray-sensitive spectrometer, which then generates different intensity values for different effective spectral values in a capture, could also be used as a detector.

After having obtained, in the steps 12 and 14, the values $I_1$ and $I_2$ by means of different effective polychromatic transmission spectrums by irradiation of the object at the same location of the object or at least at a location with the same thickness of the object, in a step 80 the value tuple P ($I_1$, $Q_{1,2}$), the value tuple P ($I_2$, $Q_{1,2}$), or the value triplet T ($I_1$, $I_2$, $Q_{1,2}$) with $I_1$=I($E_1$,d), $I_2$=I($E_2$,d) and $Q_{1,2}$=Q($E_{1,2}$,d) is ascertained, depending on according to which value tuples and/or value triplets the characteristic curves of predetermined materials are defined, which are provided in step 10, but wherein measured value tuples could also be compared with a value triplet characteristic curve. For the determination of $Q_{1,2}$, the formula explained above with reference to FIG. 1 is used, i.e.

$$Q_{1,2} = \frac{\ln(I_1)}{\ln(I_2)}.$$

The step 80 is for example performed by a computer coupled to the X-ray detector(s) 20, 28, 42, 44, 64 and also having access to the characteristic curves provided in step 10.

If necessary, the steps 12, 14, and 80 are performed at different locations of an object several times, for example at several time instants, while the object is moved past and at the same time scanned substantially perpendicularly to the optical train(s) of the arrangements of FIGS. 3a, 3b, and 3c, for example lying on a conveyor belt. The steps 12, 14, and 80 are for example repeated at a certain repetition frequency. In step 80, a value tuple or value triplet results every time. Since the objects mostly have varying thickness, the resulting value tuples or value triplets concern various, but unknown thicknesses d. In a step 82, now all these value tuples or value triplets, or the one value tuple or value triplet, are used to classify the object material. The classification in step 82 is performed on the basis of the characteristic curves from step 10 to the predetermined materials and the value tuple(s) and/or value triplet(s). By the classification, the object material is associated with one of the predetermined materials for which characteristic curves are provided in step 10. The classification in step 82 is for example carried out such that the object material is associated with that out of the predetermined materials to the characteristic curve of which the value tuple(s) or value triplet(s) of step 80 have the smallest average distance or the sum of the distance squares is minimal, or the like.

With reference to FIGS. 3a-3c, it is pointed out that, only for simplification of the illustration, only one optical train was mentioned there. Line or area cameras may, however, also be used as X-ray detectors. In this case, the object to be examined is transilluminated or examined at various locations at the same time. From a capture sequence, value tuples and/or value triplets are generated for every object point or every pixel of such an X-ray detector, wherein a different object thickness may be present for each object point in the line of object points or for each object point in the array of object points. Thus, a multiplicity of value triplets and/or value tuples, which all lie on or in the vicinity of the calibration characteristic curve of the material to be determined and may be jointly associated with the material type sought by numerical methods in step 82, already result during capture.

Furthermore, with reference to the previous description, it should be pointed out that, as already mentioned, although the evaluation of value pairs $P(I(E_1,d), Q(E_{1,2},d))$ and/or $P(I(E_2,d), Q(E_{1,2},d))$ allows for unique determination of the material, the use of the value triplet T, i.e. $T(I(E_1,d), T(I(E_2,d), Q(E_{1,2},d))$ allows for higher classification security in the step 82.

It should also be pointed out here that the use of more than two different X-ray spectrums will generally lead to an increase in the classification security. In this case, following the steps 12 and 14, a further examination step by means of a third effective polychromatic spectrum different from the two other spectrums would be performed. In this case, a value quadruple could be used, and so on.

Furthermore, it is to be pointed out that there are several ways to generate different X-ray spectrums with industrial X-ray tubes. The intensity spectrum of an X-ray tube is determined by the choice of the anode material, the acceleration voltage, as it has been described previously, but also by the subsequent beam filtering between source and detector, as it has been indicated with reference to FIG. 3c, wherein the filter then is mostly arranged before the X-ray camera. All these measures may be used for the variation of the irradiation spectrum. In the simplest case, using only one X-ray source with constant acceleration voltage, two different X-ray spectrums may be measured or used for transmission by means of different beam pre-filtering of various filter thickness or filter material type before two different X-ray cameras, as it has been described with reference to FIG. 3b. For example, the two X-ray cameras then have different sensitivity with reference to high or low X-ray energy. A difference in the center-of-gravity energy or the mean energy of the spectrum results, because the low-energy proportions of the primary X-ray intensity are for example suppressed more strongly at stronger beam filtering, whereby the beam hardening already described above arises. A further possibility for the generation of different spectrums lies in the use of two various X-ray tubes at different acceleration voltage in combination with two X-ray cameras, with which generally a greater difference in the center-of-gravity energy in the X-ray radiation can be achieved at a higher radiation intensity, wherein this embodiment has been indicated with reference to FIG. 3a.

Furthermore, it is to be noted that, although the previously described embodiments only refer to the use of X-ray radiation, the present invention may also be employed in connection with radiation types that are also suitable to examine a material by transmission or reflection of polychromatic radiation, and in which a shift of the center-of-gravity energy, and thus a shift of the effective absorption or reflection coefficient, develops by different interaction coefficients. An example for this is the use of thermal neutrons, terahertz radiation, visible radiation, infrared radiation, UV radiation, and the like.

Embodiments for classification and/or material determination methods and/or corresponding apparatuses have been described previously, independently of a corresponding application. The information arising in these methods, namely the information on the object material of which the object consists or on the material type of the examined object, may for example be used to control a mechanical material sorting apparatus, in order to achieve separation of the materials of interest. FIG. 5 refers to the illustration of such an employment.

Figure 5:
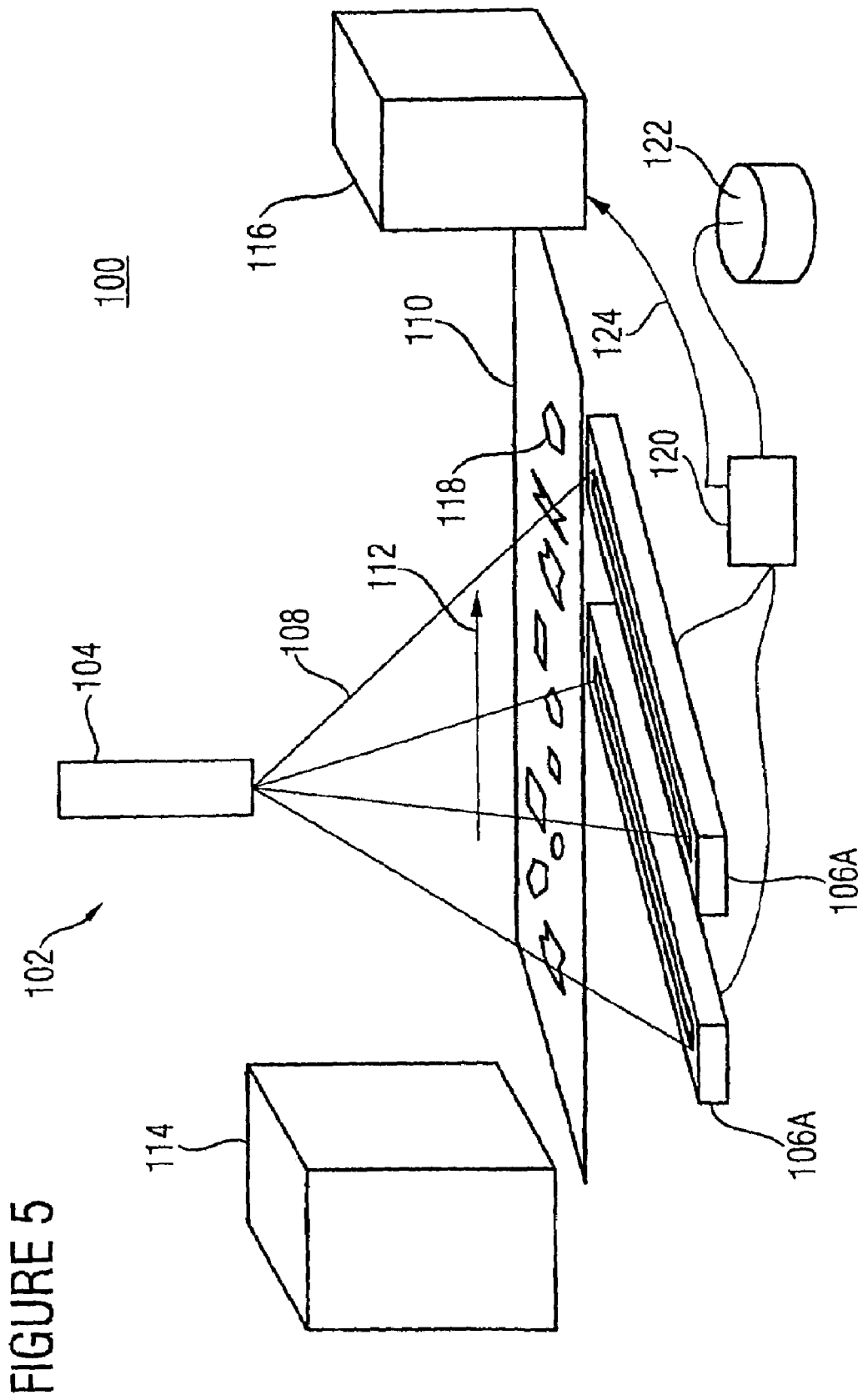
FIG. 5 is a schematic representation of an apparatus for the automatic differentiation of materials according to a further embodiment of the present invention.

FIG. 5 shows a mechanical material sorting apparatus 100 using a classification method according to FIG. 4 and an arrangement according to FIG. 3b. The apparatus 100 includes a transmission arrangement 102 comprising an X-ray tube 104 as X-ray source and two X-ray line cameras 106a and 106b as X-ray detectors according to FIG. 3b, wherein the X-ray line cameras 106a and 106b have different sensitivity characteristic curves or are sensitive in different ways to lower or higher-energy X-ray radiation from the X-ray spectrum of the X-ray tube 104. The X-ray tube 104 is arranged such that the X-ray radiation 108 impinges on the pixels of the pixel lines of both X-ray line cameras 106a and 106b. A conveyor belt 110 is placed intersecting the optical train 108 between X-ray tube 104 and line cameras 106a, 106b, such that a conveying direction 112 of the conveying means 110 passes substantially perpendicularly to the optical train 108 and furthermore substantially perpendicularly to an extension direction and/or substantially perpendicularly to the line direction of the line cameras 106a-106b. The conveyor belt 110 is arranged between a shredder 114 and a sorting station 116, for example, in order to convey shreddered object parts 118 from the shredder 114 to the sorting station 116 and, in doing so, move them through the optical trains 108 passing from the X-ray tube 104 to the individual pixels of the line cameras 106a-106b. An evaluation means 120, which is itself in turn coupled to a memory 122, in which reference data with reference to predetermined materials are provided, as it has been described with reference to step 10 of FIG. 4, is coupled to the X-ray line cameras 106a and 106b.

Having previously described the construction of the equipment 100, its functioning will be described in the following. At first, the equipment 100 is calibrated. The calibration is performed by objects 118 with different, but known materials being driven through the arrangement by means of the conveyor belt 110, and, in doing this, characteristic curves for these known materials being generated, as this has been described with reference to step 10 of FIG. 4. Particularly for an object 118 with known material, a transmission according to step 12 is obtained in this calibration by means of the line camera 106a and a measurement according to step 14 by means of the line camera 106b, namely with reference to all pixels from which the object 118 covers the connection line to the X-ray tube 104. The captures of the line cameras 106a and 106b are performed in time-shifted manner relative to each other, such that the part of the object 118 having been irradiated with the line camera 106a in the capture also is radiated through by the line camera 106b in the capture according to step 14. The evaluation means 120 then makes the determination of the value tuples and/or value triplets according to step 80. Means 120 then stores the values as the characteristic curve data in the memory 122, or as an alternative thereto, calculated parameters for analytical approximation characteristic curves. Each characteristic curve in the memory 122 is associated with an indication indicating the known material of which the object 118 by which these characteristic curve data were generated consisted.

After having generated and stored the calibration characteristic curves consisting of value triplets or value pairs for the known materials and different thicknesses, as such objects 118 mostly comprise, the equipment works in the measurement operation as described with reference to FIG. 4 by performing data captures on unknown objects 118. In particular, the unknown object 118 thus is at first scanned by the line camera 106a, in order to perform the examination according to step 12. The object 118 is scanned by the line camera in temporarily offset manner relative hereto, in order to perform the examination according to step 14. The time offset again is such that each location having been irradiated in the measurement by the line camera 106a is radiated through by the line camera 106b in the capture thereafter. Both captures lead to pairs of values $I_1$ and $I_2$ for each pixel that has been covered briefly. The processing means 120 ascertains the value tuples or value pairs according to step 80 and classifies the object material of the object 118 of unknown material according to step 82 using the characteristic curve data from the memory 122. The evaluation means 120 then sends a signal to the sorting station or the mechanical sorting means 116 over a transmission channel 124, indicating to which of the materials, for which characteristic data are filed in the memory 122, the unknown object 118 corresponds. The sorting station 116 sorts the unknown objects 118 on the conveyor belt 110 correspondingly. The evaluation means 120 outputs the signals concerning the unknown objects 118 on the conveyor belt 110 to the sorting station 116 such that the latter can suitable associate the signals on the line 124 with the objects 118 arriving on the conveyor belt 110.

In other words, the equipment 100 provides a scanning mode of operation for the practical realization of the material determination. According to FIG. 5, a transmission arrangement 102 with an X-ray source 104 and two X-ray detectors 106a and 106b is used. As already described previously, however, it is also possible to use two industrial X-ray sources operated at different acceleration voltages. Furthermore, instead of X-ray line cameras, X-ray area cameras could also be used as X-ray detectors. The line cameras 106a and 106b could comprise either only one or several pixel lines arranged successively in conveying direction 112. Such multi-line X-ray cameras could be operated in the time delay and integration mode. This means that the exposure cycles of the individual lines of these X-ray line cameras would be coordinated with the conveying speed of the conveyor 110 such that a location of the object 118 irradiated by an X-ray beam impinging on a pixel of a first line in a first capture cycle is irradiated by an X-ray beam impinging on a corresponding pixel of the next line of the line cameras in the next cycle. The resulting intensity values are summed, namely for each line of such a multi-line X-ray camera. In this manner, the integration time can be increased and/or better utilization of the transmitted X-ray radiation 108 can be achieved.

The line cameras 106a and 106b of FIG. 5 may for example be line cameras equipped with different pre-filtered entry windows. Although the line cameras in FIG. 5 are arranged perpendicularly to the movement direction 112 of the objects 118, other orientations are also completely conceivable.

It is to be pointed out that in certain cases it may be advantageous to employ area cameras instead of line cameras. Area cameras offer the advantage that an entire two-dimensional transmission image of an irradiated scene can be captured in a capture process at the same time, which might lead to a velocity advantage of the application.

The materials to be examined are preferably moved continuously by means of a conveyor belt between the X-ray source and the X-ray cameras and radiated through by the emitted X-ray radiation, 108 as it has been described previously. Likewise, using X-ray area cameras, a non-scanning application could, however, also be realized, in which the objects to be examined are examined in the resting state. If a short-time impulse X-ray tube or flash tube is employed, the objects 118 may be captured by means of area camera during the scan movement.

It is possible that the X-ray radiation 108 transmitted through the conveyor belt 110 and the object 118 is detected, converted into an electrical signal, and then digitized by the X-ray cameras 106a, 106b opposing the X-ray tube 104. The intensity values are forwarded to the evaluation means 120 and/or a data processing system, where the above-described classification algorithms are performed. The downstream mechanical separation apparatus 116 in the end effects the separation of different materials.

With reference to the embodiment of FIG. 5, it is still pointed out that the objects 118 are imaged two-dimensionally due to the lateral resolution of the X-ray cameras 106a, 106b. Thereby, in addition to the mere material discrimination, the area and the shape of the objects can be detected. From the determined material type and the transmitted intensity values, the thickness of the objects may be determined, and the volume of the objects 118 together with the area. Via the known material density, the mass of the objects can be calculated. All these calculations could be performed by the evaluation means 120. This additional information may be used in the material sorting by the sorting station 116 following further decision procedures.

With reference to the previous description, it is still pointed out that not necessarily the ratio of the logarithm of the two intensity values is used as Q value. It could also be possible that a constant is added to the logarithmic value in the denominator and/or numerator, and/or the logarithmic value in the denominator and/or numerator is multiplied and/or divided by a constant. At this occasion, it is also again pointed out that the present invention is not limited only to cases of transmission. Reflection coefficients may cause similar effects like the beam hardening described previously. In this case, "Lambert's attenuation law", which applies to the absorption but not to the reflection, is not applicable, and thus another ratio of values based on the intensity values $I_1$ and $I_2$ could be used as Q value, or another combination value on the individual intensities $I_1$ and $I_2$. In particular, the logarithm in the numerator and denominator would be eliminated.

Furthermore, it is pointed out that it is not substantial for the present invention, whether the polychromatic radiation includes a continuous spectrum or a discontinuous spectrum. It is only substantial that the effective spectrum comprises at least two spectral lines and/or two radiation frequencies. These at least two radiation frequencies preferably have at least a distance greater than 5%, 10%, or more of a center frequency of the effectively operative spectrum, i.e. the product of the spectrum used for irradiation and the sensitivity characteristic curve, or more than 5% or 10% of the lower of the two radiation frequencies. In this context, with particle radiation such as in the case of thermal neutrons, radiation frequency is supposed to mean the frequency corresponding to the energy of the corresponding particles according to the wave-particle dualism.

In other words, the previous embodiments have thus shown an apparatus and/or a method for the automatic, contactless determination of materials, using industrial X-ray sources with a means for generating X-ray transmission images at different X-ray source acceleration voltages and different sensitivity to high and lower X-ray energies, a means for the generation and storage of calibration data on the basis of known materials, a means for the calculation of the value triplets and a means for the calculation of the smallest numerical distance of the calculated value triplets to stored material characteristic curves.

In particular, it is pointed out that, depending on the circumstances, the inventive scheme for material recognition and/or classification may also be implemented in software. The implementation may be on a digital storage medium, in particular a floppy disk or CD with electronically readable control signals capable of cooperating with a programmable computer system so that the corresponding method is executed. In general, the invention thus also consists in a computer program product with program code stored on a digital storage medium for performing the inventive method, when the computer program product is executed on a computer. In other words, the invention may thus also be realized as a computer program with program code for performing the method, when the computer program is executed on a computer.

While this invention has been described in terms of several preferred embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

What is claimed is:

1. An apparatus for determining an object material of which an object consists, comprising:
    an irradiator-receiver pair for irradiating the object and receiving a resulting radiation with a first polyfrequent effective spectrum, transmitted through the object or reflected from the object, in order to obtain a first intensity value, and for irradiating the object and receiving a resulting radiation with a second polyfrequent effective spectrum, transmitted through the object or reflected from the object, in order to obtain a second intensity value, wherein the first polyfrequent effective spectrum differs from the second polyfrequent effective spectrum;
    a provider for providing reference data for a plurality of predetermined materials; and
    a processor for associating the object material with one of the predetermined materials on the basis of the reference data, a combination value based on the first and the second intensity value, as well as at least one of the first and second intensity values,
    wherein the provider is formed to store, for each predetermined material, a characteristic curve associating a respective value for the combination value based on the first and the second intensity value, with values for the at least one of the first and second intensity values, and
    wherein the processor comprises a determiner for determining which of the characteristic curves a vector of the combination value as well as the at least one of the first and second intensity values, or a plurality of vectors of the combination value and the at least one of the first and second intensity values, obtained from a plurality of irradiations/detections on the object by the irradiator-receiver pair, lies closest.

2. The apparatus of claim 1, wherein the irradiator-receiver pair comprises:
    a first radiation source for irradiating the object with polyfrequent radiation with a first polyfrequent radiation spectrum; and
    a first sensor for sensing a resulting radiation transmitted through the object or reflected from the object, wherein the first sensor is sensitive to at least two radiation frequencies within the first polyfrequent radiation spectrum.

3. The apparatus of claim 2, wherein two of the at least two radiation frequencies are spaced apart by more than 5% of a center frequency of the radiation spectrum.

4. The apparatus of claim 2, wherein the radiation source and the sensor are arranged such that the sensor senses the resulting radiation transmitted through the object.

5. The apparatus of claim 2, wherein the irradiator-receiver pair further comprises:
    a second radiation source for irradiating the object with polyfrequent radiation with a second polyfrequent radiation spectrum, wherein the first sensor is also sensitive at least at two radiation frequencies within the second radiation spectrum which differ from the at least two radiation frequencies within the first radiation spectrum.

6. The apparatus of claim 2, wherein the irradiator-receiver pair further comprises:
    a second radiation source for irradiating the object with polyfrequent radiation with a second polyfrequent radiation spectrum; and
    a second sensor for sensing a resulting radiation transmitted through the object or reflected from the object,
    wherein the second sensor is sensitive at least at two radiation frequencies within the second radiation spectrum which differ from the at least two radiation frequencies within the first radiation spectrum.

7. The apparatus of claim 2, wherein the irradiator-receiver pair further comprises:
    a second sensor for sensing a resulting radiation transmitted through the object or reflected from the object,
    wherein the second sensor is sensitive at least at two radiation frequencies within the first radiation spectrum which differ from the at least two radiation frequencies within the first radiation spectrum at which the first sensor is sensitive.

8. The apparatus of claim 2, wherein the irradiator-receiver pair further comprises:
    a second sensor for sensing a resulting radiation transmitted through the object or reflected from the object,
    wherein the first sensor differs from the second one in a sensing material, or the first and the second sensor are directly converting detectors with different discriminators.

9. The apparatus of claim 2, wherein the first radiation source is switchable so as to irradiate the object either with polyfrequent radiation with the first polyfrequent radiation spectrum or with polyfrequent radiation with a second polyfrequent radiation spectrum, the apparatus further comprising:
    a switch for switching the first radiation source so as to irradiate the object selectively with polyfrequent radiation with the first polyfrequent radiation spectrum or with polyfrequent radiation with the second polyfrequent radiation spectrum.

10. The apparatus of claim 2, wherein the irradiator-receiver pair further comprises:
- a filter set with two filters for filtering the polyfrequent radiation on the way from the first radiation source to the first sensor; and
- a changer for selectively arranging either the first or the second filter into an optical train between the first radiation source and the first sensor, wherein the two filters differ in a filter characteristic.

11. The apparatus of claim 1, wherein the irradiator-receiver pair includes an X-ray source, a thermal neutron source, a terahertz radiation source, or a light source as a radiation source.

12. The apparatus of claim 1, wherein the irradiator-receiver pair comprises an X-ray detector as sensor.

13. The apparatus of claim 1, wherein the processor is formed to ascertain the combination value based on the first and the second intensity value in a fixed manner.

14. The apparatus of claim 1, wherein the processor is formed to ascertain the combination value as a quotient of a value based on the first intensity value and a value based on the second intensity value in fixed manner.

15. The apparatus of claim 1, wherein the processor is formed to ascertain the combination value as a ratio between a logarithm of the first intensity value and a logarithm of the second intensity value.

16. The apparatus of claim 1, wherein the irradiator-receiver pair is formed to obtain a plurality of pairs of the first and the second intensity value for the object, and the processor is formed to perform the association on the basis of the reference data, combination values based on the pairs of the first and the second intensity value, and at least the first or second intensity value of the pairs of the first and the second intensity value.

17. A method of determining an object material of which an object consists, comprising the steps of:
- irradiating the object and receiving a resulting radiation with a first polyfrequent effective spectrum, transmitted through the object or reflected from the object, in order to obtain a first intensity value;
- irradiating the object and receiving a resulting radiation with a second polyfrequent effective spectrum, transmitted through the object or reflected from the object, in order to obtain a second intensity value, wherein the first polyfrequent effective spectrum differs from the second polyfrequent effective spectrum;
- providing reference data for a plurality of predetermined materials; and
- associating the object material with one of the predetermined materials on the basis of the reference data, a combination value based on the first and the second intensity value, as well as at least the first or second intensity value, wherein the step of providing comprises storing, for each predetermined material, a characteristic curve associating a respective value for the combination value based on the first and the second intensity value, with values for the at least one of the first and second intensity values, and wherein the step of associating comprises determining which of the characteristic curves a vector of the combination value as well as the at least one of the first and second intensity values, or a plurality of vectors of the combination value and the at least one of the first and second intensity values, obtained from a plurality of irradiations/detections on the object by the irradiator-receiver pair, lies closest.

18. A computer readable medium having stored thereon a computer program with program code for performing, when the computer program is executed on a computer, a method of determining an object material of which an object consists, comprising the steps of:
- irradiating the object and receiving a resulting radiation with a first polyfrequent effective spectrum, transmitted through the object or reflected from the object, in order to obtain a first intensity value;
- irradiating the object and receiving a resulting radiation with a second polyfrequent effective spectrum, transmitted through the object or reflected from the object, in order to obtain a second intensity value, wherein the first polyfrequent effective spectrum differs from the second polyfrequent effective spectrum;
- providing reference data for a plurality of predetermined materials; and
- associating the object material with one of the predetermined materials on the basis of the reference data, a combination value based on the first and the second intensity value, as well as at least the first or second intensity value, wherein the step of providing comprises storing, for each predetermined material, a characteristic curve associating a respective value for the combination value based on the first and the second intensity value, with values for the at least one of the first and second intensity values, and wherein the step of associating comprises determining which of the characteristic curves a vector of the combination value as well as the at least one of the first and second intensity values, or a plurality of vectors of the combination value and the at least one of the first and second intensity values, obtained from a plurality of irradiations/detections on the object by the irradiator-receiver pair, lies closest.

* * * * *